United States Patent
Benjamin et al.

(10) Patent No.: US 10,463,648 B2
(45) Date of Patent: *Nov. 5, 2019

(54) SUSTAINED RELEASE PHARMACEUTICAL COMPOSITIONS

(71) Applicant: Wyeth LLC, Madison, NJ (US)

(72) Inventors: Eric Joel Benjamin, Jamestown, NC (US); Wendy Ann Dulin, Tuxedo, NY (US); Yanning Lin, Lake Hiawatha, NJ (US); Kai Zhuang, River Edge, NJ (US)

(73) Assignee: Wyeth, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/058,769

(22) Filed: Aug. 8, 2018

(65) Prior Publication Data

US 2018/0344695 A1 Dec. 6, 2018

Related U.S. Application Data

(60) Continuation of application No. 15/912,438, filed on Mar. 5, 2018, now Pat. No. 10,292,966, which is a division of application No. 10/975,254, filed on Oct. 28, 2004, now abandoned.

(60) Provisional application No. 60/515,315, filed on Oct. 29, 2003.

(51) Int. Cl.
*A61K 31/407* (2006.01)
*A61K 9/20* (2006.01)
*A61K 9/28* (2006.01)

(52) U.S. Cl.
CPC .......... *A61K 31/407* (2013.01); *A61K 9/2054* (2013.01); *A61K 9/2866* (2013.01)

(58) Field of Classification Search
CPC ... A61K 9/2054; A61K 31/407; A61K 9/2866
See application file for complete search history.

(56) References Cited

U.S. PATENT DOCUMENTS

| | | |
|---|---|---|
| 4,988,679 A | 1/1991 | Chavkin et al. |
| 5,009,895 A | 4/1991 | Lui |
| 5,028,434 A | 7/1991 | Barclay et al. |
| 5,112,621 A | 5/1992 | Stevens et al. |
| 5,126,366 A | 6/1992 | Stack et al. |
| 5,166,367 A | 11/1992 | Stack et al. |
| 5,189,171 A | 2/1993 | Stack et al. |
| 5,225,206 A | 7/1993 | Fushimi et al. |
| 5,235,055 A | 8/1993 | Stack et al. |
| 5,245,051 A | 9/1993 | Stack et al. |
| 5,318,988 A | 6/1994 | Schohe-Loop et al. |
| 5,633,376 A | 5/1997 | Thurkauf et al. |
| 5,756,532 A | 5/1998 | Stack et al. |
| 5,914,263 A | 6/1999 | Buizer et al. |
| 5,962,465 A | 10/1999 | Stack et al. |
| 6,010,718 A | 1/2000 | Al-Razzak et al. |
| 6,126,970 A | 10/2000 | van 't Klooster |
| 6,218,405 B1 | 4/2001 | Birch et al. |
| 6,350,773 B1 | 2/2002 | Marquis |
| 6,417,177 B1 | 7/2002 | Nelson |
| 6,524,618 B1 | 2/2003 | Kumar et al. |
| 7,135,479 B2 | 11/2006 | Zhou et al. |
| 7,662,979 B2 | 2/2010 | Galante |
| 2001/0008903 A1 | 7/2001 | Birch et al. |
| 2002/0114836 A1 | 8/2002 | Maillard |
| 2005/0095292 A1 | 5/2005 | Benjamin et al. |
| 2007/0190129 A1 | 8/2007 | Ahmed et al. |
| 2018/0193311 A1 | 7/2018 | Benjamin et al. |

FOREIGN PATENT DOCUMENTS

| | | |
|---|---|---|
| AU | 2004/286855 | 4/2011 |
| CN | 1155546 | 7/1997 |
| EP | 0771800 A2 | 5/1997 |
| JP | H02-003608 | 1/1990 |
| JP | H09-249671 | 9/1997 |
| JP | H09-315969 | 12/1997 |
| JP | H11-509539 | 8/1999 |
| WO | WO 1991/13872 A1 | 9/1991 |
| WO | WO 1997/003670 | 2/1997 |

(Continued)

OTHER PUBLICATIONS

Application Technology of Pharmaceutically Used Auxiliary Materials, 2nd Ed., Huimin Hou et al., Chinese Medical Technology Publishing House, Beijing, 2002, p. 200-204 and p. 209-212.

(Continued)

*Primary Examiner* — Michael G. Hartley
*Assistant Examiner* — Leah H Schlientz
(74) *Attorney, Agent, or Firm* — Knobbe, Martens, Olson & Bear LLP

(57) ABSTRACT

The present invention provides controlled release dosage formulations of compounds having the Formula:

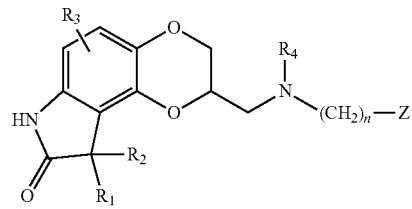

or pharmaceutically acceptable salts thereof, and in particular, aplindore. The dosage forms are useful, inter alia, for reducing side effects from administration of such compounds.

28 Claims, No Drawings

(56) References Cited

FOREIGN PATENT DOCUMENTS

| WO | WO 1998/29415 | 7/1998 |
|----|---------------|--------|
| WO | WO 1998/43646 | 10/1998 |
| WO | WO 2001/41750 A2 | 6/2001 |
| WO | WO 2005/044262 | 5/2005 |

OTHER PUBLICATIONS

Applied Pharmacokinetics—Principles of Therapeutic Drug Monitoring, William J. Jusko, "Guidelines for Collection and Analysis of Pharmacokinetic Data," (1992) Ch. 2, pp. 2-1 through 2-43.
Bagul et al., Current Status of Tablet Disintegrants: A Review, (1996) 1-9, at http://www.pharmainfo.net/exclusive/reviews/current_status_of_tablet_disintergrants:a_review/.
Cheng et al., Schizophrenia and drug delivery systems, J Drug Target, (2000) 8(2):107-17.
Dange et al., Comparison of Bioavailability and Pharmacodynamics of DilIndian J Physiol Pharmacol., (1992) 36(3):205-208.
[Farmacia Práctica Remington vol. 2, 17 Ed. Editorial Medica Panamericana, Capitulo VIII, Preparados Farmacéuticos y su Elaboración] (pp. 2223-2229).
Filip et al., Treatment of extrapyramidal side effects with terguride. Psychiatry Res. (1992) 41(1):9-16.
Glenn et al., Twenty years of pharmacology, J Head Trauma Rehabil. (2005) 20(1):51-61.
Gordon et al., In vivo and in vitro evaluation of four different aqueous polymeric dispersions for producing an enteric coated tablet, Int'l J Pharma. (1995) 115(1): 29-34.
Human Pharmacology: Molecular to Clinical, K. Kist, ed. (Mosby-Year Books: Philadelphia) 1991.
Ishii et al., Structure and Synthesis of Arnottin I: a 6H-Benzo[d]naphtho[1.2-b]pyran-6-one Derivative from a Plant Source, J Chem Soc-Perkin Transactions 1, (1993) 9:1019-1022.
Lindenmayer et al., New pharmacotherapeutic modalities for negative symptoms in psychosis. Acta Psychiatrica Scand., (1995) 92 (Supp. 388):15-19.
Keith, S., Advances in psychotropic formulations, Prog Neuropsychopharmacol Biol Psychiatry (2006) 30(6):996-1008.
Ennis et al., Novel indolodioxanes with antihypertensive effects: potent ligands for the 5-HT1A receptor. J Med Chem. (1992) 35(16):3058-3066.
Principles of Drug Action: The Basis of Pharmacology, 3rd., W.B. Pratt & P. Taylor, eds., (Churchill Livingstone: New York) 1990.
Remington's Pharmaceutical Sciences, 18th Ed., Gennaro, ed., (Mack Publishing Co., Easton, PA) 1990.
Remington: The Science and Practice of Pharmacy, 20th edition, chapter 47, pp. 1047-1060, 2000.
Svensson et al., Partial dopamine receptor agonists reverse behavioral, biochemical and neuroendocrine effects of neuroleptics in the rat: potential treatment of extrapyramidal side effects. Neuropharmacology (1993) 32(10):1037-1045.
Svensson T.H. et al., Effects of 5-HT2- and DA-D2-receptor antagonists on the mesolimbocortical DA system assessed by electrophysiology and microdialysis. Schizophrenia Res. (1993) 9(2,3):253.
International Search Report dated Apr. 29, 2005 for International Application No. PCT/US2004/036013.
Office Action dated May 7, 2015 in corresponding Argentine Patent Application No. P040103986.
Windholz et al. [Eds.], The Merk Index—An Encyclopedia of Chemicals, Drugs, and Biologicals, 10th Edition, No. 4480, pp. 662/663.

SUSTAINED RELEASE PHARMACEUTICAL COMPOSITIONS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation of U.S. patent application Ser. No. 15/912,438, entitled "SUSTAINED RELEASE PHARMACEUTICAL COMPOSITIONS" and filed Mar. 5, 2018, which in turn is a divisional of U.S. patent application Ser. No. 10/975,254, entitled "SUSTAINED RELEASE PHARMACEUTICAL COMPOSITIONS" and filed Oct. 28, 2004, which in turn claims priority to U.S. Provisional Application No. 60/515,315, filed Oct. 29, 2003, which is incorporated herein by reference in its entirety.

BACKGROUND OF THE INVENTION

Field of the Invention

This invention relates to sustained release formulations of dopaminergic compounds, including S-2-[(Benzylamino)-methyl]-2,3,8,9-tetrahydro-7H-1,4-dioxino[2,3-e]indol-8-one (aplindore) and pharmaceutically acceptable salts thereof.

Description of the Related Art

Compounds having the 2-(Aminomethyl)-2,3,8,9-7H-4-dioxino[2,3-e]-indol-8-one structure have been reported to have significant activity at the dopamine receptor, as well as the ability to modulate dopamine synthesis. See U.S. Pat. No. 5,756,532, incorporated by reference herein in its entirety for all purposes. These compounds are useful in the treatment and prevention of a variety of dopaminergic disorders including schizophrenia, schizoaffective disorder, symptoms of Parkinson's disease, Tourette's syndrome, psychosis in Lewis Body disease, psychosis in Alzheimer's disease, hyperprolactinemia, drug addiction and acute mania in bipolar disorder. The potent and selective D2/D3 partial agonist aplindore (S-2-[(Benzylamino)-methyl]-2,3,8,9-tetrahydro-7H-1,4-dioxino[2,3-e]indol-8-one) has been identified as a treatment for schizophrenic patients.

The administration of aplindore results in high initial drug concentrations. Such an "immediate release" pattern can pose difficulties, which include failure to maintain optimal exposure levels over time, and unpleasant side effects from having too large initial dose. Thus, there is a significant need for controlled release aplindore formulations capable of increasing $T_{max}$ and/or decreasing $C_{max}$ without reducing overall drug exposure. This invention is directed to these, as well as other, important ends.

SUMMARY OF THE INVENTION

In some embodiments, the present invention provides controlled release dosage formulations comprising a compound of Formula I:

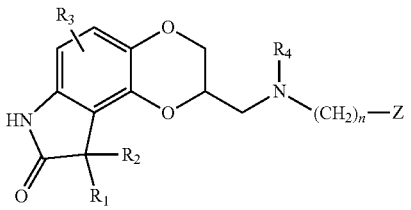

wherein:
$R^1$ and $R^2$ are, independently, hydrogen, alkyl of 1 to 6 carbon atoms, phenyl or benzyl;
or $R^1$ and $R^2$, taken together, are benzylidene optionally substituted with $R^3$ as defined below or alkylidene of up to 6 carbon atoms;
or $R^1$ and $R^2$, taken together with the carbon to which they are attached, form a carbonyl moiety or a cycloalkyl group having three to 6 carbon atoms;
$R^3$ is hydrogen, hydroxy, halo, trifluoromethyl, trifluoromethoxy, alkyl of 1 to 6 carbon atoms, alkoxy of 1 to 6 carbon atoms, arylalkoxy of 7 to 12 carbon atoms, alkanoyloxy of 2 to 6 carbon atoms, amino, mono- or di-alkylamino in which each alkyl group has 1 to 6 carbon atoms, alkanamido of 2 to 6 carbon atoms or alkanesulfonamido of 1 to 6 carbon atoms;
$R^4$ is hydrogen or alkyl of 1 to 6 carbon atoms;
n is one of the integers 0, 1, 2, 3, 4, 5, or 6;
Z is hydrogen, hydroxy, alkyl of 1 to 6 carbon atoms, alkenyl of 2 to 6 carbon atoms, alkynyl of 2 to 6 carbon atoms, alkoxy of 1 to 6 carbon atoms, cycloalkyl of 3 to 8 carbon atoms, polycyclic alkyl of 7 to 15 carbon atoms, phenyl optionally substituted with $R^3$ as defined above, phenoxy optionally substituted with $R^3$ as defined above, naphthyl optionally substituted with $R^3$ as defined above or naphthyloxy optionally substituted with $R^3$ as defined above, heteroaryl or heteroaryloxy, in which the heterocyclic ring of the heteroaryl or heteroaryloxy group is selected from thiophene, furan, pyridine, pyrazine, pyrimidine, indole, indazole, imidazole, chroman, coumarin, carbostyril, quinoline, benzisoxazole, benzoxazole, pyrazole, pyrrole, thiazole, oxazole, or isoxazole and the heterocyclic ring is optionally substituted by $R^3$ as defined above;
or a pharmaceutically acceptable salt thereof.

In some preferred embodiments, the compound is 2-[(Benzylamino)-methyl]-2,3,8,9-tetrahydro-7H-1,4-dioxino[2,3-e]indol-8-one, or a pharmaceutically acceptable salt thereof. In some especially preferred embodiments, the compound is S-2-[(Benzylamino)-methyl]-2,3,8,9-tetrahydro-7H-1,4-dioxino[2,3-e]indol-8-one (aplindore), or a pharmaceutically acceptable salt thereof:

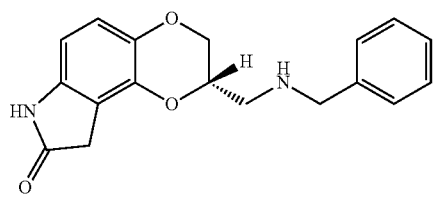

Aplindore

In some preferred embodiments of each of the controlled release dosage formulations described herein, the compound is aplindore fumarate.

In some embodiments, the controlled release dosage formulation is an oral dosage formulation.

In some embodiments, the formulation comprises one or more microparticles, which can be, for example, pellets, beads, tablets, spheroids or combinations of two or more thereof.

In some embodiments of the oral controlled release dosage formulations of the invention, the compound is released from said dosage form at a rate effective to increase the time it takes to reach maximum therapeutic concentration (i.e., $T_{max}$) as compared to the $T_{max}$ of an instant release formulation, for example, so that the $T_{max}$ of the controlled release dosage formulation is at least about 1.5 times, 2 times, 2.5 times, 3 times, 4 times, 5 times or 5.5 times the $T_{max}$ of an instant release formulation.

In some embodiments, the compound is released from said dosage form at a rate effective to decrease the maximum therapeutic concentration of said compound (i.e., $C_{max}$) compared to the $C_{max}$ of an instant release formulation, for example, so that the $C_{max}$ of the controlled release dosage formulation is less than about 0.75 times, 0.60 times, 0.50 times, or 0.40 times the $C_{max}$ of an instant release formulation.

In some embodiments, the compound is released from the dosage form at a rate effective to increase the pharmaceutically effective concentration of the compound in a mammal over a time period (i.e., area under the plasma (serum or blood) concentration versus time curve, AUC, such as $AUC_{0-12}$) relative to an instant release formulation, for example, so that the $AUC_{0-12}$ of the controlled release dosage formulation is at least about 1.05 times, 1.1 times 1.2 times, 1.3 times, or 1.4 times the $AUC_{0-12}$ of the instant release formulation.

In some embodiments, the compound is released from a 0.1 mg dosage form at a rate effective to provide an area under the plasma (serum or blood) concentration versus time curve (AUC) from zero to twelve (12) hours ($AUC_{0-12}$) from about 260 pg*h/ml to about 2400 pg*h/ml; while for other such embodiments the $AUC_{0-12}$ is from about 290 pg*h/ml to about 1300 pg*h/ml. AUC can be measured as described in *Principles of Drug Action: The Basis of Pharmacology*, 3rd ed., W. B. Pratt & P. Taylor, eds., (Churchill Livingstone: New York), 1990. In some embodiments, 5 mg of the compound provides an $AUC_{ss}$ (area under the curve at steady state, from 0 to 12 hours) from about 36000 pg*h/ml to about 109000 pg*h/ml; while others provide an $AUC_{ss}$ from about 36000 pg*h/ml to about 75000 pg*h/ml. In some embodiments, 30 mg of the compound provides an $AUC_{0-12}$ from about 121000 pg*h/ml to about 890000 pg*h/ml, while other such embodiments provide an $AUC_{0-12}$ from about 170000 pg*h/ml to about 760000 pg*h/ml.

In some embodiments, the compound is released from 0.1 mg dosage form at a rate effective to provide a maximum plasma (serum or blood) concentration ($C_{max}$) from about 40 pg/ml to about 190 pg/ml; and in other such embodiments from about 40 pg/ml to about 180 pg/ml. Maximum plasma concentration is measured as described in *Principles of Drug Action: The Basis of Pharmacology*, 3rd ed., W. B. Pratt & P. Taylor, eds., (Churchill Livingstone: New York), 1990; Human Pharmacology: Molecular to Clinical, K. Kist, ed. (Mosby-Year Books: Philadelphia), 1991. In some embodiments, 5 mg of the compound provides a $C_{max}$ from about 4000 pg/ml to about 14000 pg/ml, while in other such embodiments, the $C_{max}$ is from about 6000 pg/ml to about 12000 pg/ml. In some embodiments, 30 mg of the compound provides a $C_{max}$ from about 18000 pg/ml to about 110000 pg/ml; in other such embodiments, the $C_{max}$ is from about 20000 pg/ml to about 92000 pg/ml.

In some embodiments, dosages are gradually increased (i.e., titrated) over time (e.g., days or weeks) to the desired dosage to avoid or lessen the severity of possible side effects such as nausea or other indications of patient intolerability. For example, some embodiments of the present invention provide for the administration of increasing dosages incrementally where the starting dose ranges from about 0.05 mg to about 0.4 mg per day. In other embodiments, the dosages are increased incrementally over a period of time to an ending dose, which it or a dose of a greater amount is administered on a daily basis thereafter, and which may range for example, from about 2 mg to about 75 mg per day. In other embodiments, the dose titration period to reach the ending dose is at least about 3 days, at least about 5 days, at least about 12 days, or at least about 15 days.

In other embodiments, a set of controlled release dosage forms, which comprise a plurality of individual controlled release dosage forms, where two or more of the individual dosage forms comprise different amounts of the compound. The individual dosage form may be a single unit dosage (e.g., one tablet or capsule), or may include multiple unit dosages (e.g., 2 or more tablets or capsules). In some embodiments, the set of controlled release dosage formulations has 2 or more individual controlled release dosage forms containing a starting dose and an ending dose (where the ending dose or a dose of a greater amount is administered on a daily basis thereafter and the ending dose is greater than the starting dose). For example, the set may contain two or more different individual controlled release dosage forms ranging from about 0.05 mg to about 30 mg of compound. In other embodiments, the set of controlled release dosage formulations have at least two or more of the individual controlled release dosage forms selected from 0.05 mg, 0.1 mg, 0.2 mg, 0.25 mg, 0.3 mg, 0.4 mg, 0.5 mg, 0.6 mg, 0.75 mg, 1 mg, 1.5 mg, 2 mg, 3 mg, 4 mg, 5 mg, 6 mg, 8 mg, 10 mg, 11 mg, 12 mg, 13 mg, 14 mg, 15 mg, 16 mg, 17 mg, 20 mg, 23 mg, 24 mg, 25 mg, 26 mg or 30 mg of the compound.

In some embodiments, the set of controlled release dosage formulations has at least two of the individual controlled release dosage forms containing a different amount of the compound with the amount of the compound in each of the different dosage forms differing by at least ten percent, and more preferably at least 20 percent. In other embodiments, each of the individual dosage forms provides an $AUC_{0-12}$ ranging from about 260 pg*h/ml to about 890000 pg*h/ml.

In some embodiments, the oral controlled release dosage formulations include at least some of microparticles, which include an inert core; a layer of the active compound disposed on the inert core; and a coating comprising at least one release rate controlling polymer disposed on the layer of the compound. In some embodiments, all of the microparticles include the inert core, the layer of compound, and the coating.

In some embodiments, the oral controlled release dosage formulations include at least some of microparticles, which include an inert core; a coating layer disposed on the inert core, the coating layer including the compound and at least one release rate controlling polymer. In some embodiments, all of the microparticles include the inert core and the coating layer.

In further embodiments, the oral controlled release dosage formulations include at least some of microparticles, which include a core that includes the active compound; and a coating layer disposed on the core, the coating layer including at least one release rate controlling polymer. In some embodiments, all of the microparticles include the core that includes the compound, and the coating layer.

In some embodiments, the oral controlled release dosage formulations include at least some of microparticles, which include a core, the core including the compound and at least one release rate controlling polymer; and a coating layer disposed on the core, the coating layer optionally including at least one release rate controlling polymer. In some embodiments, all of the microparticles include the core that includes the compound and the coating layer.

In some embodiments of the oral controlled release dosage formulations of the invention, the percentage by weight of the active compound in the formulation is from about 1% to about 25%, preferably from about 2% to about 15%, preferably from about 5% to about 10%.

In some embodiments of the oral controlled release dosage formulations of the invention, the formulation includes capsules containing the microparticles. In some embodiments, the microparticles are compressed into a tablet or a pellet.

In some embodiments, the oral controlled release dosage formulations include one or more pellets. In some embodiments, the pellets further include a coating that further includes at least one release rate controlling polymer. In some embodiments, the pellets are contained within a capsule.

In some embodiments of the oral controlled release dosage formulations of the invention, the formulation further includes one or more ingredients selected from fillers, disintegrants, excipients, and combinations of two or more thereof. In some embodiments, the pellets and ingredients are compressed into tablets.

In some embodiments of the controlled release dosage formulations of the invention, the percentage by weight of the active compound in the formulation is from about 1% to about 25%, preferably from about 2% to about 15%, preferably from about 5% to about 10%.

In some embodiments of the oral controlled release dosage formulations of the invention, the formulation comprises a wax matrix, preferably wherein the formulation is a tablet. In some such embodiments, the wax is present in a total amount by weight of from about 10% to about 60%, preferably from about 20% to about 40%, preferably.

In some embodiments, the wax includes carnauba wax, cetostearyl alcohol, fatty acids, or a mixture or two or more thereof. In some embodiments, the wax-containing formulation further includes at least one release rate-controlling polymer.

In some embodiments, the oral controlled release dosage formulation is a tablet further including a coating that includes a water soluble polymer, and/or at least one release-rate controlling polymer.

In some embodiments, the oral controlled release dosage formulations of the invention include a polyethylene oxide matrix, preferably wherein the formulation is a tablet. In some embodiments, the tablet includes a polyethylene oxide matrix.

In some embodiments, the polyethylene oxide is present in a total amount by weight of from about 5% to about 40%, preferably from about 10% to about 20%, of the formulation.

In some embodiments, the oral controlled release dosage formulation is a tablet that includes at least one release rate controlling polymer. In some preferred embodiments, the dosage form is a co-compressed tablet. In some preferred embodiments, the co-compressed tablet includes a core and an outer compressed coat; wherein the core includes active compound and at least one release rate controlling polymer. In further embodiments, the co-compressed tablet includes a core and an outer compressed coat; wherein the compressed coat includes active compound and at least one release rate controlling polymer. In some preferred embodiments, the co-compressed tablet includes a core and an outer compressed coat; wherein each of the core and the compressed coat includes active compound and at least one independently selected release rate controlling polymer. In some preferred embodiments, the core and the outer compressed coat each contain at least one high viscosity matrix forming hydroxypropyl methyl cellulose, and at least one low viscosity matrix forming hydroxypropyl methyl cellulose. Preferably, the low viscosity matrix forming polymer comprises a hydroxypropyl methylcellulose selected from Methocel K100LV, Methocel E50LV, Methocel E5, Methocel E15LV or a combination of two or more thereof; and the high viscosity matrix forming polymer includes a hydroxypropyl methylcellulose selected from Methocel K4M, Methocel K15M, Methocel K100M, Methocel E4M and combinations of two or more thereof. In some especially preferred embodiments, the low viscosity matrix forming polymer includes Methocel K100LV, and the high viscosity matrix forming polymer includes Methocel K4M.

In some embodiments of the oral controlled release dosage formulations of the invention, the formulation includes at least one matrix forming polymer, which preferably is selected from waxes, gums, hydroxypropyl methylcelluloses, hydroxyethyl celluloses, hydroxypropyl celluloses, carbapols, polymethacrylates, polyethylene oxides, and combinations of two or more thereof.

In some embodiments of the oral controlled release dosage formulations of the invention, the active compound is present in an amount of from about 0.02% to about 16% by weight, preferably from about 0.02% to about 4% by weight of the formulation.

In some embodiments of the controlled release dosage formulations of the invention, the formulations include one high viscosity hydroxypropyl methyl cellulose and one low viscosity hydroxypropyl methyl cellulose. Preferably, the high viscosity matrix forming polymer includes a hydroxypropyl methylcellulose selected from Methocel K4M, Methocel K15M, Methocel K100M, Methocel E4M and combinations of two or more thereof. Preferably, the hydroxypropyl methylcellulose is present in an amount by weight of from about 15% to about 80%, preferably about 25% to about 50%, and is preferably Methocel K4M. Preferably, the low viscosity hydroxypropyl methyl cellulose includes Methocel K100LV, Methocel E50LV, Methocel ES, Methocel E15LV or a combination of two or more thereof, preferably in an amount by weight of from about 15% to about 80%, preferably from about 20% to about 50%, and is preferably Methocel K100LV.

In some embodiments, the oral controlled release dosage formulations of the invention can include a water soluble excipient, preferably in an amount by weight of up to about 50%, preferably from about 2% to about 25%. In some preferred embodiments, the excipient is a sugar.

In some embodiments, the oral controlled release dosage formulations of the invention can include a water dispersing excipient, which is preferably microcrystalline cellulose, colloidal silicone dioxide, silicified microcrystalline cellulose, starch, a super disintegrant, or a combination of two or more thereof. Preferably, the water dispersing excipient is present in an amount by weight of from about 2% to about 50%, preferably from about 5% to about 25%.

In some embodiments, the oral controlled release dosage formulations of the invention include one or more of antioxidants, stabilizers, chelating agents, acidic pH modifiers, basic pH modifiers, or combinations of two or more thereof.

In some embodiments, the oral controlled release dosage formulations of the invention include one or more of a binder, a flow aid, lubricant, or a solubility modifier, which can be a surfactant, an acidic compound or a basic compound.

In some embodiments the oral controlled release dosage formulations of the invention include a coating that includes a water soluble polymer and a coloring agent, and/or a pH dependent release rate controlling polymer, a pH independent release rate controlling polymer, or a combination thereof.

In some of the foregoing oral controlled release dosage formulations of the invention, the dosage form includes one or more release rate controlling polymers, which can be, for example, one or more of polymethacrylates, methacrylic acid-methacrylic acid ester copolymers, cellulose acetate phthalate, ethyl cellulose, polyvinyl acetate-phthalate, hydroxypropylmethylcellulose phthalate, or combinations of two or more thereof. In some preferred embodiments, the release rate controlling polymer can be one or more of polymethacrylates, methacrylic acid-methacrylic acid ester copolymers, ethyl cellulose, or combinations of two or more thereof.

In further embodiments, the release rate controlling polymer is selected from high viscosity matrix forming hydroxypropyl methyl celluloses and low viscosity matrix forming hydroxypropyl methyl celluloses.

In some embodiments, the high viscosity matrix forming polymer comprises a hydroxypropyl methylcellulose selected from Methocel K4M, Methocel K15M, Methocel K100M, Methocel E4M and combinations of two or more thereof.

In some embodiments, the low viscosity matrix forming polymer comprises a hydroxypropyl methylcellulose selected from Methocel K100LV, Methocel E50LV, Methocel E5, Methocel E15LV or a combination of two or more thereof.

In some embodiments, the release rate controlling polymer comprises of one or more of Eudragit RS, Eudragit RL, Surelease, or combinations of two or more thereof.

In some embodiments, the oral controlled release dosage formulations of the invention include one or more solubility modifiers, for example surfactants, acidic compounds, basic compounds, and combinations thereof.

In some embodiments, the oral controlled release dosage formulations of the invention include one or more of antioxidants, pH modifiers, metal chelators, or combinations of one or more thereof.

In further embodiments, the oral controlled release dosage formulations of the invention can include one or more of fillers, disentegrants, binders, or combinations of one or more thereof.

In some embodiments, the oral controlled release dosage formulations of the invention include one or more fillers, binders, disintegrants, lubricants, stabilizers, pH modifiers, antioxidants or combinations of two or more thereof.

In some preferred embodiments, the oral controlled release dosage formulations of the invention include a pharmaceutically effective amount of an active compound; a high viscosity hydroxypropyl methyl cellulose in an amount of from about 20% to about 60% by weight; and a low viscosity hydroxypropyl methyl cellulose in an amount of from about 20% to about 60% by weight.

In some further embodiments, the oral controlled release dosage formulations of the invention include a pharmaceutically effective amount of an active compound, a water soluble compensating excipient in an amount of from about 0.5% to about 5% by weight; a water dispersible excipient in an amount of from about 5% to about 30% by weight; a high viscosity hydroxypropyl methyl cellulose in an amount of from about 20% to about 60% by weight; a low viscosity hydroxypropyl methyl cellulose in an amount of from about 20% to about 60% by weight; and, optionally, a lubricant in an amount of from about 0.1% to about 1% by weight.

In some further preferred embodiments, the oral controlled release dosage formulations of the invention include a pharmaceutically effective amount of an active compound; a water dispersible excipient in an amount of from about 10% to about 30% by weight; a high viscosity hydroxypropyl methyl cellulose in an amount of from about 20% to about 40% by weight; a low viscosity hydroxypropyl methyl cellulose in an amount of from about 20% to about 40% by weight; and, optionally, a lubricant in an amount of from about 0.1% to about 1% by weight.

In some embodiments the present invention provides methods of treating a disorder of the dopaminergic system that include administering to a patient in need of such treatment a controlled release dosage formulation according to the invention.

In some further embodiments, the present invention provides methods for the treatment of schizophrenia, schizoaffective disorder, Parkinson's disease, Tourette's syndrome, psychosis in Lewis Body disease, psychosis in Alzheimer's disease, hyperprolactinemia, drug addiction or acute mania in bipolar disorder, comprising administering to a patient in need of such treatment a controlled release dosage formulation according to the invention.

In some further embodiments, the present invention provides methods for the treatment of symptoms of Parkinson's disease, comprising administering to a patient in need of such treatment a controlled release dosage formulation according to the invention.

The present invention also provides processes for preparing the formulations provided herein, and products of those processes.

DETAILED DESCRIPTION OF THE PREFERRED EMBODIMENT

The present invention provides controlled release dosage formulations that include as an active ingredient a compound of Formula I:

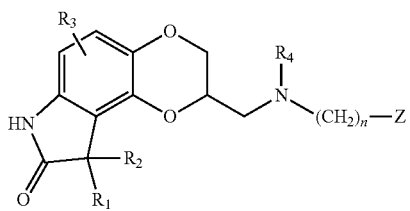

wherein the constituent variables are as described supra.

As used herein, the term "active compound" is intended to refer to compounds of Formula I, and particularly 2-[(Benzylamino)-methyl]-2,3,8,9-tetrahydro-7H-1,4-dioxino[2,3-e]indol-8-one, S-2-[(Benzylamino)-methyl]-2,3,8,9-tetrahydro-7H-1,4-dioxino[2,3-e]indol-8-one (aplindore), and their pharmaceutically acceptable salts, preferably but not limited to their fumarate salts, and prodrugs of the foregoing.

The dosage formulations described herein facilitate the controlled release of active compounds in a mammal through many routes, including oral administration. In some preferred embodiments, the formulations include the compound S-2-[(Benzylamino)-methyl]-2,3,8,9-tetrahydro-7H-1,4-dioxino[2,3-e]indol-8-one, referred to as aplindore, preferably the fumarate salt thereof.

Aplindore may form pharmaceutically acceptable salts with various acids including inorganic acids such as hydrochloric acid, hydrobromic acid, phosphoric acid, perchloric acid, nitric acid, iodic acid, and the like as well as organic acids such as oxalic acid, fumaric acid, succinic acid, acetic acid, benzoic acid, glycolic acid, malic acid, citric acid, methane sulfonic acid, benzene sulfonic acid, salicyclic acid, para-toluene sulfonic acid, adipic acid, and the like. Formulations including all such salts are within the scope of the present invention.

As used herein, the term "prodrug" has its accustomed meaning of a covalently modified derivative of a compound or a pharmaceutically acceptable salt thereof, wherein such modification results in a derivative that is metabolically labile and after administration to a mammal, and results in liberation of the parent compound in the gut, plasma or tissue. Such derivatives may be prepared by esterification, acylation or otherwise modifying the compound in such a way as to incorporate a physiologically labile group.

Aplindore contains one chiral center and is used predominately as the S-isomer. However, activity also resides in the R-isomer. The formulations of the present invention include both isomers, and are not limited to a single enantiomer or particular enantiomeric mixture.

For purposes of this invention, the terms "instant release", "instant release formulation" refer to formulations that provide a rapid and non-gradual release of active compound from the formulation; i.e., formulations that contain active compound and a rapidly dissolving carrier that does not retard the release of the active compound from the formulation. Such instant release formulation are either devoid of release rate controlling polymers or other species that retard the release of the active compound from the formulation, or contain such polymers or species in amounts that are sufficiently small such that the release of the active compound from the formulation is not retarded relative to an otherwise identical formulation lacking such polymers or species. One example of such an "instant release" formulation is active compound blended in the microcrystalline cellulose Avicel, which results in greater than 75% dissolution of aplindore or a pharmaceutically acceptable salt thereof in less than 0.25 hours in a 0.1 N HCl solution as described infra.

The terms "slow release", "medium release" and "fast release" are controlled release formulations as described herein, above, that release active compound at a rate that is slow, medium or fast rate relative to each other.

As used herein, the terms "controlled release", "controlled release formulation", "controlled release dosage formulation" and the like refer to formulations that contain materials that retard the release of active compound from the formulation relative to an "instant release" formulation as described above, e.g., relative to an otherwise identical formulation lacking the release rate controlling polymer or other release-retarding materials. Thus, the term "controlled release" can apply to any number of extended release forms and will be considered substantially synonymous with delayed release, time release, prolonged release, time programmed release, time released, time coated release, sustained release, slow acting, long acting, delayed acting, spaced release, time spaced release, extended acting, extended action, and the like.

It will be appreciated that controlled release formulations can result in a release of active compound from the dosage form at a rate effective to increase the time it takes to reach maximum therapeutic concentration (i.e., $T_{max}$) as compared to the $T_{max}$ of an instant release formulation, for example, so that the $T_{max}$ of the controlled release dosage formulation is at least about 1.5 times, 2 times, 2.5 times, 3 times, 4 times, 5 times or 5.5 times the $T_{max}$ of an instant release formulation. Controlled release formulations can also result in release of active compound from the dosage form at a rate to decrease the maximum therapeutic concentration of said compound (i.e., $C_{max}$) compared to the $C_{max}$ of an instant release formulation, for example, so that the $C_{max}$ of the controlled release dosage formulation is less than about 0.75 times, 0.60 times, 0.50 times, or 0.40 times the $C_{max}$ of an instant release formulation. Controlled release formulations can also result in release of the active compound from the dosage form at a rate effective to increase the pharmaceutically effective concentration of the compound in a mammal over a time period (i.e., area under the plasma (serum or blood) concentration versus time curve, AUC, such as $ALIC_{0.12}$) relative to an instant release formulation, for example, so that the $ALIC_{0.12}$ of the controlled release dosage formulation is at least about 1.05 times, 1.1 times 1.2 times, 1.3 times, or 1.4 times the ALICo.12 of the instant release formulation.

"$C_{max}$." "$T_{max}$." and "ALIC" values reported herein, unless stated as being "mean" values, refer to the values observed in an individual patient. Moreover, $C_{max}$. $T_{max}$. and ALIC values, unless otherwise stated, may be values observed at steady state when dosing at regular time intervals (e.g., every 12 hours) for multiple days (e.g., multiple dose administration) or values for a single dose administration.

As used herein, the term "release rate controlling polymer" is intended to denote any polymer material suitable for pharmaceutical dosage forms that retard the release of drug substances from such dosage forms. Examples of suitable release rate controlling polymers can be found in *Remington's Pharmaceutical Sciences,* 18th Ed., Gennaro, ed., Mack Publishing Co., Easton, Pa., 1990), incorporated by reference herein in its entirety for all purposes. Some preferred release rate controlling polymers: suitable for use in the present invention include, without limitation, one or more of polymethacrylates, methacrylic acid-methacrylic acid ester copolymers, cellulose acetate phthalate, ethyl cellulose, polyvinyl acetate-phthalate, hydroxypropylmethylcellulose phthalate, high viscosity matrix forming hydroxypropyl methyl celluloses such as Methocel K4M, Methocel K15M, Methocel K100M, Methocel E4M, and low viscosity matrix forming hydroxypropyl methyl celluloses such as Methocel K100LV, Methocel E50LV, Methocel E5, Methocel E15LV or a combination of two or more thereof. Further preferred release rate controlling polymers include one or more of Eudragit RS, Eudragit RL, Surelease, or combinations of two or more thereof.

It will be appreciated that the different release rate controlling polymers confer different release rate properties to the formulation. By varying the type and amount of such polymers in the formulation, a wide variety of release profiles of active compound can be achieved. Those skilled in the art are credited with the ability to select appropriate polymers in appropriate amounts to achieve desired release rates of active compound.

Controlled release solid formulations of aplindore, or pharmaceutically acceptable salts of aplindore, can include any of the many dosage forms known in the art, including tablets, for example co-compressed tablets and matrix tablets, encapsulated dosage forms such as capsules or pellets containing microparticles in the form of pellets, beads, tablets, spheroids or combinations of two or more thereof, powders and the like.

In accordance with some preferred embodiments, the controlled release formulation can contain microparticles that contain active compound, and at least one release rate controlling polymer in a location suitable to retard release of the active compound. Such microparticles can be in the form of, for example, pellets, beads or spheroids. In some embodiments, the microparticles include a core and at least one coating layer. Either of the core and the coating layer can either be inert (i.e., contain no active compound) or can contain active compound, provided that at least one of the core or one coating layer contain active compound. In some embodiments, the microparticles are contained within a capsule, or compressed into a tablet.

The microparticulate dosage formulations of the invention can contain active compound in any convenient percentage by weight. Typically, the formulation contains active compound in percentage by weight of from about 1% to about 25%, preferably from about 2% to about 15%, preferably from about 5% to about 10%.

In addition to active compound and release rate controlling polymer, the formulations of the invention can contain any of a variety of additional materials that confer beneficial properties to the formulation. Such materials include, for example, solubility modifiers such as surfactants, acidic compounds and basic compounds, antioxidants, acidic and basic pH modifiers, chelating agents, fillers, disentegrants, binders, lubricants, stabilizers, excipients including water soluble excipients such as sugars and water dispersing excipients such as microcrystalline cellulose, colloidal silicone dioxide, silicified microcrystalline cellulose and starch.

Nonlimiting examples of water soluble or water dispersing excipients include lactose, mannitol, sucrose, and the like. The water soluble excipients may be present in a range depending upon the particular therapeutic objective required. In general, the range of water soluble excipients is from 0 to 50%, or 2 to 25%. Examples of water dispersible excipients include microcrystalline cellulose, colloidal silicone dioxide, silicified microcrystalline cellulose (Prosolve), starches, superdisintegrants such as croscarmellose sodium and the like. The range of water dispersible excipients is typically from about 5% to about 50%, preferably from about 10% to about 30% by weight.

Non-limiting examples of stabilizers include antioxidants such as BHA, BHT, ascorbic acids, tocopherols, and the like. Nonlimiting examples of suitable metal chelators include EDTA, citric acid and the like. Nonlimiting examples of pH modifiers that are either acidic or basic compounds such as citric acid, sodium citrate, fumaric acid, sodium fumarate and the like. Nonlimiting examples of binders include starches, PVP, HPMC, HPC and the like. Nonlimiting examples flow aids include magnesium stearate and the like. Nonlimiting examples of solubility modifiers include surfactants like SLS or Tween 80, and the like.

In some preferred embodiments, the formulations of the invention are in the form of coated pellets or spheres. One nonlimiting example of such formulations is spheres containing a core of active compound in an inert matrix, coated with a release rate controlling polymer as disclosed herein. Nonlimiting examples of a suitable release rate controlling polymers are pH dependent or independent polymers, such as polymethacrylates Eudragit US, Eudragit RS/RL, cellulose acetate phthalate, ethyl cellulose and the like. Further examples include one or more of high viscosity matrix forming hydroxypropyl methyl cellulose, and low viscosity matrix forming hydroxypropyl methyl celluloses as described herein.

In some embodiments, the formulations of the invention are in the form of pellets. Examples of such formulations include those containing pellets that contain a layer of active compound on top of an inert core, for example a sugar sphere, and a surface coating containing one or more release rate controlling polymers.

In some embodiments, the formulations of the invention are in the form of tablets. In some such embodiments, the percentage by weight of active compound in the formulation is from about 1% to about 25%, preferably from about 2% to about 15%, preferably from about 5% to about 10%. Nonlimiting examples of such tablets are co-compressed tablets (i.e., a "tablet-in-tablet), and matrix tablets.

Typically, the co-compressed tablet includes a core and an outer compressed coat. Either or both of the core and the outer compressed coat can contain active compound and/or one or more release rate controlling polymers. In some preferred embodiments, the dosage form is a co-compressed tablet wherein both the core and the outer compressed coat contain active compound, and at least one, preferably two, release rate controlling polymers, one of which is preferably a high viscosity matrix forming hydroxypropyl methyl cellulose, and the other of which is preferably a low viscosity matrix forming hydroxypropyl methyl celluloses. Preferred high viscosity matrix forming polymers include a hydroxypropyl methylcellulose selected from Methocel K4M, Methocel K15M, Methocel K100M, Methocel E4M and combinations of two or more thereof, preferably Methocel K4M. Preferred low viscosity matrix forming polymers include hydroxypropyl methylcelluloses selected from Methocel K100LV, Methocel E50LV, Methocel E5, Methocel E15LV or a combination of two or more thereof, preferably Methocel K100LV.

In some preferred embodiments, the tablet is a matrix tablet. The matrix forming composition may contain waxes, gums, polyethylene oxides, carbapols, hydroxypropyl methylcelluloses, hydroxyethyl celluloses, polymethacrylates or other release rate controlling polymers as described herein. In some embodiments, such matrix tablets are prepared by blending the active compound and the matrix forming polymer together, and compressing the blend.

In some embodiments, the tablet is a matrix tablet that includes a wax matrix. Such tablets maybe prepared by, for example, by melting a wax such as carnauba wax, cetostearyl alcohol or fatty acids, or combinations thereof, and adding active compound along with a filler such as microcrystalline cellulose as well as other excipients, fillers, lubricants and the like, and allowing the mixture to cool. The formulations prepared maybe optionally coated with or contain one or more water soluble or release rate controlling control release polymers. Typically, the wax is present in the formulation in a total amount by weight of from about 10% to about 60%, preferably from about 20% to about 40%, preferably from about 10% to about 60%. A wide variety of suitable waxes are amenable to the present invention. Nonlimiting examples of such waxes include carnauba wax, cetostearyl alcohol, fatty acids, or a mixture or two or more thereof. The matrix tablet also can contain one or more release rate-controlling polymers as described herein.

A further nonlimiting example of such a matrix tablet is a tablet that includes a polyethylene oxide matrix, for example and not limitation, polyethylene oxide resins such as SENTRY POLYOX (Union Carbide Corp.) or equivalents. Suitable POLYOX's include POLYOX WSR N-10, N-60 K, WSR-1105N, WSR 303. The POLYOX used may have a molecular weight in the range of 100,000 to 7,000,000 or 900,000 to 5,000,000. Typically, the polyethylene oxide is present in the formulation in a total amount by weight of from about 5% to about 40%, preferably from about 10% to about 20% of the formulation. The matrix tablet also can contain one or more release rate-controlling polymers as described herein.

A further nonlimiting example of such a matrix tablet is a tablet that includes one or more release rate controlling polymers as described herein as the matrix forming polymer. In some preferred embodiments, such tablets include one or more high viscosity matrix forming hydroxypropyl methyl celluloses, and/or one or more low viscosity matrix forming hydroxypropyl methyl celluloses as described herein as the matrix forming polymer. In some preferred embodiments, it is advantageous to use a high viscosity hydroxypropyl methylcellulose such as Methocel K4M at an amount by weight of from about 15% to about 80%, preferably about 25% to about 50%. Other high viscosity polymers may also be used such as Methocel K15M, Methocel K100M, or Methocel E4M and the like. In some embodiments, a low viscosity hydroxypropyl methylcellulose is used such as MethocelE50LV, Methocel E5, or MethocelE15LV or combinations thereof and the like. In certain embodiments, both a high viscosity and a low viscosity hydroxypropyl methylcellulose are used in the matrix together wherein the low viscosity hydroxypropyl methylcelluloses is present in a range of from about 15% to 80%, preferably from about 25% to about 50%, and the high viscosity hydroxypropyl methylcellulose is present in an amount by weight of from about 20% to about 50%.

In general, active compound may be contained within any layer of a dosage form of the invention, and controlled release of the active compound can be achieved by the use of a release rate controlling polymer either contained within the layer containing the active compound, or in any layer encompassing the layer containing the active compound, for example an enteric coating. Such an enteric coating may also be applied to pellets, beads or spheroids containing active compound, or the active compound can be contained within the enteric coating itself.

In some embodiments the controlled release dosage formulation is a matrix tablet formulation where the active compound is present in an amount by weight of from about 0.02% to about 16%, preferably from about 0.02% to about 4%.

The tablets of the formulations of the invention can be coated with water soluble polymer coloring agents, or coated with pH dependent or pH independent polymers to further control the rate of release of active compound. In some embodiments, the tablets of this invention are coated with a subcoat, an enteric coating or an overcoating, or any combination thereof.

The types of formulations contemplated by the present invention are not limited to the examples presented herein. Rather, the examples indicate that a vast number of formulations fulfill the general goal of the invention and one of ordinary skill in the art will recognize that varying the formulations beyond those of the examples is contemplated where the formulation so varied still accomplishes the general goal of the invention by providing a controlled release of active compound.

In especially preferred embodiments of each of the formulations of the invention, the active compound is aplindore. Aplindore and pharmaceutically acceptable salts thereof are particularly well-suited to treating various disorders of the central nervous system and more particularly to those central nervous disorders relating to the dopaminergic system. Because aplindore (or any drug) requires a sufficient exposure level to achieve its desired effects, the drug must be dosed in a manner sufficient to achieve the particular blood plasma level over a period of time deemed sufficient to meet the clinical objective sought. However, it has been discovered that in certain cases, dosing of subject patients with aplindore resulted in side effects including nausea and vomiting which has been correlated with the time period where aplindore reached its maximal plasma levels. Simply reducing the dose would not always be satisfactory since, while the side effects might lessen or disappear, the overall drug exposure levels might not be satisfactory to treat the particular condition. Rather, what is desired is a treatment regimen that maintains or increases the efficacy of the drug, but does not provide the relatively large initial blood concentration seen with administration of instant release dosages of aplindore.

Thus, in accordance with the present invention there, are provided controlled release dosage forms that ameliorate the deleterious side effects of instant release aplindore administration, including oral and non-oral controlled release dosage formulations. Accordingly, the present invention includes each of the numerous technologies that exist for controlled release non-oral dosage formulations including pumps, implants, patches, depot injection, injection with controlled release carrier, and the like. Delivery of active compound in accordance with the present invention can be via mucosal, vaginal, rectal, ocular, transdermal, intrauterine, routes and the like.

In other embodiments, it has been found desirable to gradually increase the dosage of aplindore in a mammal to a desired dosage over a period of time (i.e., titrate) to reduce initial possible side effects of aplindore. Thus, the present invention provides a method of administering aplindore that includes administering to a mammal in need thereof a starting controlled release dosage formulation comprising aplindore; and thereafter administering to the mammal at least one other controlled release dosage formulation comprising aplindore, wherein the starting controlled release dosage formulation contains a lesser amount of aplinodre relative to the other controlled release dosage formulation. In some embodiments, the starting controlled release dosage formulation comprises from about 0.05 mg to about 0.4 mg of aplindore.

Also included in accordance with the present invention are any of the numerous technologies that exist for attaining sustained release oral formulations including those described above, as well as micro and macroencapsulation, fibers, matrices both polymeric (high viscosity and low viscosity) and non-polymeric, foams, liposomes, micelles, gels, physically dispersed drug in polymeric, porous, slightly porous or non-porous matrices, adsorption onto ion exchange resins, mixing with or adsorption onto chemically or biologically degradable matrices and the like. The active compound can be formulated in such a way that the drug achieves a single maximal concentration or may be formulated so that the drug is pulsed in two or more peaks. Oral delivery maybe via way of liquid or solid dosage form.

Liquid dosage forms include syrups, suspensions, emulsions, elixirs and the like. The liquid carrier can include an organic or aqueous base and maybe further modified with suitable pharmaceutical additives such as solubilizers, emulsifiers, buffers, preservatives, sweeteners, flavoring agents, suspending agents, thickening agents, colorsviscosity regulators, stabilizers or osmoregulators, or combinations thereof. The aqueous carrier may also contain polymeric substances or oils.

While the present invention has been described with specificity in accordance with certain of its preferred embodiments, the following examples serve only to illustrate the invention and are not intended to limit the same.

EXAMPLES

The following examples illustrate some controlled release dosage formulations that achieve the invention objective by decreasing the rate of dissolution, increasing the time to maximum concentration, or reducing the maximum concentration value for a given quantity of aplindore, or a combination of these three. The following non-limiting examples of oral delivery vehicles formulated for controlled delivery are listed below. The examples are illustrated for non-limiting dose ranges of 0.05 to 10 mg and a wide range of controlled release oral formulations in order to demonstrate a number of release profiles that were further tested in monkeys and humans and reported on herein below.

The three formulation approaches illustrated below are 1) coated pellets; 2) co-compressed tablets (tablet-in-tablet); and 3) matrix tablets.

Coated Pellets:

A low required dose of aplindore or its pharmaceutically acceptable salts allows for layering of the drug onto the surface of an inert sugar sphere, followed by a release-controlling polymer coat. The drug may also be incorporated into the sphere by an extrusion/spheronization process which is not illustrated in the present examples.

Co-Compressed Tablets:

The use of a co-compressed tablet was investigated for the purpose of having a zero-order or nearly zero-order release profile and different release profiles obtained by varying the amounts of drug and polymer (HPMC) in the core tablet and in the outer compressed coat, as well as the total tablet weight. Tablets can be made individually via various presses or equipment well known to those of skill in the art. The co-compressed tablets of the present invention were made individually on the Carver press using standard round tooling.

Matrix Tablets:

Matrix tablet examples were prepared utilizing hydroxypropyl methylcelluslose (HPMC), waxes, polyethylene oxides (PEO), alone or in combinations.

In order to make the aplindore directly compressed tablets easy to swallow and to avoid any esophagus irritation, 3 wt % Opadry II White was coated on the aplindore core tablets.

Example 1

Sustained Release Aplindore Fumarate Pellets Prepared Using Extrusion/Spheronization and SR Coating Batches were made by blending drug with Microcrystalline Cellulose (Avicel PH102) and granulating with water to form a wet mass. The wet mass was extruded through a 1.0 mm screen and spheronized on a small Caleva system. The formulations and the dissolution data in 0.1 N HCl for the uncoated pellets are presented in Table 1. The Avicel matrix does not retard the release of aplindore and essentially all of the drug is released from the uncoated pellets in 30 minutes.

TABLE 1

Formulation and Dissolution of Uncoated Pellets

| | Composition | |
| --- | --- | --- |
| | 1 | 2 |
| Aplindore (% listed as free base) | 5.0% | 10.0% |
| Avicel PH 102 | 95.0% | 90.0% |
| Dissolution (Hrs) | % Dissolved | % Dissolved |
| 0.1N HCl | | |
| 0.25 | 76.91 | 85.90 |
| 0.5 | 91.12 | 90.30 |
| 1 | 94.79 | 91.07 |
| 2 | 94.13 | 90.86 |

The spheres prepared by extrusion/spheronization were coated with Eudragit RS/RL and Surelease to control the release of aplindore. The formulation and the dissolution profiles are shown in Table 2. The Surerelease coated spheres of composition 3 were tested in monkeys to assess the in vivo release and the corresponding monkey plasma levels are shown in Table 3.

TABLE 2

Formulation and dissolution of sustained release coated spheres prepared by extrusion/spheronization.

| | Composition | |
| --- | --- | --- |
| | 3 % W/W | 4 % W/W |
| Spheroids core | | |
| Aplindore fumarate | 10.0 | 5.0 |
| Avicel | 90.0 | 95.0 |
| SR Coating | | |
| Surerelease | 7.5 | 0 |
| 80:20Eudragit RS/Eudragit RL | 0 | 15 |
| Dissolution (Hrs) | % Dissolved | % Dissolved |
| 0.1N HCl | | |
| 0.25 | 1.3 | na |
| 0.5 | 11.3 | na |
| 1 | 28.49 | na |
| 2 | 45.78 | na |
| pH 6.8 phosphate buffer | | |
| 1 | 19.53 | 3.78 |
| 2 | 38.88 | 24.30 |
| 4 | 53.3 | na |
| 6 | na | 77.10 |
| 8 | 62.11 | 97.7 |
| 12 | 65.38 | 99.38 |

Example 2

Sustained Release Aplindore Fumarate Pellets Prepared by Sustained Release Coating of Layered Sugar Spheres Aplindore fumarate sustained-release pellets were also prepared by layering the active drug on sugar spheres. The formulation and the dissolution data are given in Table 3. Composition 5 was tested for in vivo release in monkeys. The data is included in Table 4.

TABLE 3

Formulation and dissolution of sustained release coated aplindore layered sugar spheres.

|  | Composition 5 % W/W |
|---|---|
| Spheroids core |  |
| Sugar spheres 25/30 mesh | 100 |
| Drug coating (5% as free base) |  |
| aplindore fumarate | 44.4 |
| HPMC 6 cps | 55.6 |
| Controlled release Coating |  |
| Eudragit RS100 | 45.5 |
| Triethylcitrate | 9.1 |
| Talc | 45.5 |
| Dissolution Time (Hr) | % Dissolved |
| 0.1N HCl |  |
| 0.25 | 0.9 |
| 0.5 | 3.77 |
| 1 | 13.71 |
| 2 | 31.1 |
| pH 6.8 phosphate |  |
| 1 | 8.15 |
| 2 | 21.27 |
| 4 | 38.37 |
| 8 | 63.89 |
| 12 | 79.02 |

TABLE 4

Summary Aplindore Bioavailability Parameters in Monkeys

| Composition | Description | AUC (ng * hr/mL) | Cmax (ng/mL) | Tmax (hr) | % Relative Bioavailability |
|---|---|---|---|---|---|
| 6 | Instant Release capsule | 1290 | 166.8 | 2.5 | 100 |
| 3 | Surelease coated spheres | 369.0 | 19.72 | 14.7 | 29 |
| 7 | Eudragit RS/RL coated spheres | 1205 | 96.28 | 4.7 | 85 |
| 5 | Eudragit RS coated layered spheres | 1051 | 83.77 | 5.3 | 76 |
| 8 | Tablet-in-tablet | 1097 | 98.87 | 4.0 | 85 |
| 9 | Wax matrix | 854.6 | 52.33 | 6.3 | 80 |
| 10 | HPMC matrix | 1219 | 52.17 | 4.0 | 85 |

Example 3

Sustained Release Tablets Prepared Using Co-Compression Method

The use of a co-compressed tablet was investigated for the purpose of having a zero-order or nearly zero-order release profile. Different release profiles could be obtained by varying the amounts of drug and polymer (HPMC) in the core tablet and in the outer compressed coat, as well as the total tablet weight. All tablets were made individually on the Carver press using standard round tooling. The formulations and the dissolution data are given in Table 5. In vivo absorption data in Monkeys for Composition 8 are included in Table 4.

TABLE 5

Formulations for Aplindore Fumarate Co-Compressed Tablets (Tablet-in-Tablet):

|  | 8 ||
|---|---|---|
| INGREDIENTS: | Inner | Outer |
| Aplindore (as base) | 5.000 | 5.000 |
| Lactose, Spray dried | 25.800 | 68.250 |
| Avicel, PH 101 | 25.800 | 68.250 |
| Methocel K4M Prem CR | 36.000 | 48.000 |
| Methocel K100 Prem LV | 7.000 | 59.500 |
| Mg-stearate | 0.400 | 1.000 |
| Total | 100.000 | 250.000 |
| Dissolution (Hrs) | % Dissolved ||
| pH 6.8 phosphate buffer |  |  |
| 0.25 | 5.50 ||
| 0.50 | 8.47 ||
| 1 | 12.98 ||
| 1 | 12.98 ||
| 2 | 19.70 ||
| 4 | 27.99 ||
| 6 | 34.54 ||
| 8 | 41.63 ||
| 12 | 55.72 ||

Example 4

Wax Matrix Tablets

Table 6 lists formulations of matrix tablets containing Carnauba wax and cetostearyl alcohol as matrix forming polymers, with microcrystalline cellulose. The wax was melted and aplindore alone or its blend with microcrystalline cellulose was added with stirring. The mixture was allowed to cool to room temperature and milled. The resulting granulation was blended with the lubricant magnesium stearate and compressed into tablets. The tablets exhibit sustained release profile.

TABLE 6

Wax matrix formulations and dissolution

| | Composition | |
|---|---|---|
| | 9 % W/W | 11 % W/W |
| Aplindore fumarate | 4.0 | 4.0 |
| Avicel PH101 | 63.0 | 55.5 |
| Carnauba wax | 32.0 | — |
| Cetostearyl alcohol | — | 40 |
| Magnesium stearate | 1.0 | 0.5 |
| Dissolution (Paddle 50 rpm, phosphate buffer pH 6.8). | % Dissolved | % Dissolved |
| 0.25 | 6.56 | 7.46 |
| 0.5 | 10.23 | 10.33 |
| 1 | 21.13 | 15.87 |
| 2 | 53.8 | 27.43 |
| 4 | 72.36 | 45.26 |
| 6 | 77.02 | 56.81 |
| 8 | 79.01 | 64.64 |
| 12 | 81.50 | 76.19 |

Example 5

Polyethylene Oxide Matrix Tablets

Table 6 outlines formulations and dissolution profiles of matrix tablets prepared using PEO polymers. The tablets show sustained release profiles.

TABLE 6

Wax and polyoxyethelene oxide matrix formulations and dissolution

| | Composition | |
|---|---|---|
| | 12 % W/W | 13 % W/W 4.0 |
| Aplindore fumarate | 4.0 | 40.75 |
| Avicel PH101 | 40.75 | 40.75 |
| Lactose | 40.75 | — |
| Polyoxyethylene oxide (PEO WSR N-60K) | 10 | 10 |
| Polyoxyethylene oxide (PEO WSR N-301K) | — | 0.5 |
| Magnesium stearate | 0.5 | |
| Dissolution (Paddle 50 rpm, phosphate buffer pH 6.8). | % Dissolved | % Dissolved |
| 0.25 Hr | 20.42 | 18.74 |
| 0.5 | 29.18 | 25.73 |
| 1 | 41.92 | 37.5 |
| 2 | 58.58 | 51.47 |
| 4 | 77.61 | 69.93 |
| 6 | 88.11 | 81.6 |
| 8 | 92.52 | 88.11 |
| 12 | 95.48 | 91.67 |

Example 6

Hydroxypropyl Methylcellulose Matrix 10 Mg Tablets

The type of hydroxypropyl methylcellulose used in accordance with examples of the invention are hydroxypropylmethylcellulose sold under the trademark METHOCEL (Dow Chemical Co.) or equivalents. Suitable METHOCELS include the K grades such as METHOCEL K15M Premium CR, METHOCEL K100M Premium CR, METHOCEL K100 Premium LV and METHOCEL K4M Premium. Other suitable METHOCELS include the E, F and J grades.

Table 7 lists examples of matrix tablets utilizing hydroxypropyl methylcellulose (HPMC) of low viscosity Methocel KLV100 (hydroxypropyl content less than 9%) and high viscosity Methocel K4M. Aplindore fumarate and the polymers were mixed, lubricated with magnesium stearate and compressed into tablets. These tablets show sustained release dissolution in 0.1 N HCl and pH 6.5 buffer.

In order to make the aplindore fumarate tablets easy to swallow and to avoid any esophagus irritation, 3 wt % Opadry 11 White was coated on the aplindore fumarate core tablets.

The aplindore 10 mg fast-release, 10 mg medium-release and 10 mg slow-release HPMC matrix core tablets were tested in monkeys along with an immediate-release capsule formulation. The formulations and dissolution data are listed in Table 7. Tablets were compressed using 11/32 inch standard concave round tooling. The dissolution was determined as directed in the USP, using Apparatus 2 (paddles), at 50 rpm using 0.1N HCl for the first 2 hours and 0.05 M phosphate buffer, pH 6.8 at 37±0.5° C. Volume of dissolution medium was 900 ml.

The pharmacokinetic parameters are presented in Table 8. These aplindore medium-release and slow-release formulations have achieved the requirement according to their in vivo performance in the monkey study. The bioavailabilities of the three HPMC matrix tablet formulations were 85.5, 95.0 and 116.4% respectively, for slow-release, medium-release and fast-release formulations relative to the immediate-release capsule formulation.

TABLE 7

Composition and Dissolution of APLINDORE 10.0 MG Fast-Release, Medium-Release and Slow-Release HPMC Matrix Tablets

| | Compositions | | | |
|---|---|---|---|---|
| | Composition 10 Slow Release Tablets | Composition 14 Medium Release Tablets | Composition 15 Fast Release Tablets | Composition 16 Immediate Release Capsules (reference) |
| APLINDORE free base (added as fumarate salt) | 4%* | 4%* | 4%* | 265%** |
| Lactose Fast Flo | 16.70% | 20% | 66.60% | 0% |

TABLE 7-continued

Composition and Dissolution of APLINDORE 10.0 MG Fast-Release, Medium-Release and Slow-Release HPMC Matrix Tablets

| | | | | |
|---|---|---|---|---|
| Pregelatinized Starch LM | 0% | 0% | 0% | 58.86% |
| Avicel PM 301 | 16.70% | 20% | 0% | 37.99% |
| Methocel K4M Prem CR | 29% | 29% | 29% | 0% |
| Methocel K100LV Prem CR LH | 33.20% | 26.60% | 0% | 0% |
| Mg stearate | 0.40% | 0.40% | 0.40% | 0.50% |
| Total Tablet Weight | 250 mg | 250 mg | 250 mg | 275 mg |
| Tablet Hardness | >20 kp | 10-13 kp | 10-13 kp | |
| Tabletting Machine | Carver Press | Colton | Colton | |

| Dissolution Time (HR) | % Dissolved | % Dissolved | % Dissolved | % Dissolved |
|---|---|---|---|---|
| 0.17 | N/A | N/A | N/A | 79.27 |
| 0.33 | N/A | N/A | N/A | 98.45 |
| 0.5 | 10.77 | 14.67 | 18.3 | 100.64 |
| 0.75 | N/A | N/A | N/A | 101.18 |
| 1 | 16.19 | 23.25 | 29.25 | N/A |
| 2 | 25.37 | 37.44 | 45.26 | N/A |
| 4 | 37.25 | 55.07 | 64.91 | N/A |
| 8 | 53.69 | 77.08 | 89.96 | N/A |
| 12 | 66.97 | 89.55 | 101.79 | N/A |

*Amount adjusted based on purity of the aplindore fumarate salt. Corresponding adjustment with lactose is made.

**Amount adjusted based on purity of the aplindore fumarate salt. Corresponding adjustment with Pregelatinized Starch LM is made.

TABLE 8

Bioavailability Parameters for 10 mg APLINDORE Sustained Release Matrix Tablets in Monkeys

| Composition | Description | AUC (ng*hr/mL) | Cmax (ng/mL) | Tmax (hr) | HVD (hr) | % Relative Bioavailability |
|---|---|---|---|---|---|---|
| 6 | IR capsules | 1290 | 166.8 | 2.5 | 6.4 | 100 |
| 10 | Slow Release | 1219 | 62.17 | 4.0 | 20.6 | 85 |
| 15 | Fast Release | 1242 | 99.07 | 2.3 | 15.1 | 116 |
| 14 | Medium Release | 1355 | 98.93 | 5.3 | 15.0 | 95 |

Example 7

Controlled Release Matrix 5.0 mg, 2.0 mg, 0.5 mg and 0.05 mg Tablets

Four different strengths 5.0 mg, 2.0 mg, 0.5 mg and 0.05 mg were developed for each of the medium-release and slow-release formulation. It was desirable that the in vivo plasma profiles are similar to those of the 10 mg medium and slow release formulations shown in table 7.

The tablet shapes and total tablet weights were kept same for all four different strengths and for the two different release rate tablets. There is a large difference between the strengths of these tablets, therefore, for the highly water-soluble aplindore fumarate, it is difficult to formulate the four doses by only changing the proportion of HPMC polymer levels. This was accomplished by compensating the amount of the reduction of water-soluble active drug by adding a commonly used highly water-soluble excipient, while keeping other excipients with the same proportions. In the formulations of aplindore fumarate 5.0 mg, 2.0 mg, 0.5 mg and 0.05 mg medium and slow release formulations, Lactose Fast Flo has been chosen as the water-soluble compensating excipient. Lactose Fast Flo is highly water-soluble and has good flow and compaction properties. It has been used in the 10.0 mg medium release formulation.

The aplindore fumarate 5.0 mg, 2.0 mg, 0.5 mg and 0.05 mg medium-release, and slow-release HPMC matrix tablets were all made on the Colton Press. The formulations were finalized based on dissolution results at 150 rpm and are listed in Tables 9 and 10.

The dissolution data of aplindore fumarate 5.0 mg, 2.0 mg, 0.5 mg and 0.05 mg medium-release & 5.0 mg, 2.0 mg, 0.5 mg and 0.05 mg slow-release HPMC matrix tablets are also listed in Table 9 and 10.

TABLE 9

Composition and Dissolution of Aplindore Fumarate
5.0 mg, 2.0 mg, 0.5 mg and 0.05 mg Medium-Release HPMC
Matrix Tablets in pH 6.8 Buffer with USP II Method with Paddle Speed at 150 rpm

|  | Compositions | | | |
| --- | --- | --- | --- | --- |
|  | Composition #17 5.0 mg Medium Release | Composition #18 2.0 mg Medium Release | Composition #19 0.5 mg Medium Release | Composition #20 0.05 mg Medium Release |
| aplindore free base* (added as fumarate salt) | 2.00% | 0.80% | 0.20% | 0.02% |
| Lactose Fast Flo | 22.00% | 23.20% | 23.80% | 23.98% |
| Avicel PH 301 | 20.00% | 20.00% | 20.00% | 20.00% |
| Methocel K4M, Prem CR | 29% | 29.00% | 29.00% | 29.00% |
| Methocel K100LV, Prem CR LH | 26.60% | 26.60% | 26.60% | 26.60% |
| Mg stearate | 0.40% | 0.40% | 0.40% | 0.40% |
| Dissolution Time (HR) | % Dissolved Paddle Speed at 150 rpm | % Dissolved Paddle Speed at 150 rpm | % Dissolved Paddle Speed at 150 rpm | % Dissolved Paddle Speed at 50 rpm |
| 0.5 | 10.26 | 17.55 | 19.8 | 8.03 |
| 1 | 16.4 | 18.28 | 23.19 | 13.83 |
| 2 | 31.78 | 31.81 | 36.7 | 20.56 |
| 4 | 51.32 | 51.72 | 54.43 | 33.17 |
| 8 | 75.07 | 73.66 | 79.03 | 50.59 |
| 12 | 89.95 | 91.25 | 94.51 |  |

*Amount adjusted based on purity of the aplindore fumarate salt. Corresponding adjustment with lactose is made.

TABLE 10

Composition and Dissolution of Aplindore Fumarate
5.0 mg, 2.0 mg, 0.5 mg and 0.05 mg Slow-Release HPMC Matrix
Tablets in pH 6.8 Buffer with USP II Method with Paddle Speed at 150 rpm

|  | Compositions | | | |
| --- | --- | --- | --- | --- |
|  | Composition #21 5.0 mg Slow Release | Composition #22 2.0 mg Slow Release | Composition #23 0.5 mg Slow Release | Composition #24 0.05 mg Slow Release |
| Aplindore free base* (added as fumarate salt) | 2.00% | 0.80% | 0.20% | 0.02% |
| Lactose Fast Flo | 2.00% | 3.20% | 3.80% | 3.98% |
| ProSolv HD 90 | 20.50% | 20.50% | 20.50% | 20.50% |
| Methocel K4M, Prem CR | 40% | 40.00% | 40.00% | 40.00% |
| Methocel K100LV Prem CR LH | 35.10% | 35.10% | 35.10% | 35.10% |
| Mg stearate | 0.40% | 0.40% | 0.40% | 0.40% |
| Dissolution Time (HR) | % Dissolved Paddle Speed at 150 rpm | % Dissolved Paddle Speed at 150 rpm | % Dissolved Paddle Speed at 150 rpm | % Dissolved Paddle Speed at 50 rpm |
| 0.5 | 5.58 | 4.5 | 11.25 | 7.22 |
| 1 | 12.11 | 14.25 | 14.26 | 11.4 |
| 2 | 21.69 | 28.9 | 22.95 | 17.85 |
| 4 | 40.2 | 40.23 | 36.74 | 28.6 |
| 8 | 59.53 | 80.79 | 59.05 | 44.69 |
| 12 | 77.39 | 76.07 | 72.59 | N/A |

*Amount adjusted based on purity of the aplindore fumarate salt. Corresponding adjustment with lactose is made.

Example 8

HPMC Matrix Tablets Film Coating

In order to make aplindore fumarate HPMC matrix tablets easier to swallow, Opadry and enteric coatings were applied on the active core tablets and the bioavailabilities were found to be comparable (data not shown)

Example 9

Further Formulations and Processes

Further formulations for aplindore core tablets are shown in the table below.

TABLE 11

Aplindore Fumarate Medium-Release Formulations (core tablets)

| | Compositions | | | | |
|---|---|---|---|---|---|
| | aplindore | aplindore | aplindore quantity | aplindore | aplindore |
| | 10.0 mg | 5.0 mg | 2.0 mg<br>type | 0.5 mg | 0.05 mg |
| | Medium Release | Medium Release | Medium Release | Medium Release | Medium Release |
| APLINDORE free base* (added as fumarate salt) | 4.00% | 2.00% | 0.80% | 0.20% | 0.02% |
| Lactose Fast Flo | 20.00% | 22.00% | 23.20% | 23.80% | 23.98% |
| Avicel PH 301 | 20.00% | 20.00% | 20.00% | 20.00% | 20.00% |
| Methocel K4M, Prem CR | 29.00% | 29.00% | 29.00% | 29.00% | 29.00% |
| Methocel K100LV Prem CR LH | 26.60% | 26.60% | 26.60% | 26.60% | 26.60% |
| Mg stearate | 0.40% | 0.40% | 0.40% | 0.40% | 0.40% |
| Total | 100% | 100% | 100% | 100% | 100% |
| Total Tablet Weight | 250 mg | 250 mg | 250 mg | 250 mg | 250 mg |

*Aplindore at 72.8% patency. Actual amount is based on actual potency of aplindore.
Corresponding adjustment with Lactose is made.

TABLE 12

Aplindore Slow-Release Formulation (core tablets)

| | Compositions | | | | |
|---|---|---|---|---|---|
| | aplindore | aplindore | aplindore quantity | aplindore | aplindore |
| | 10.0 mg | 5.0 mg | 2.0 mg<br>type | 0.5 mg | 0.05 mg |
| | Slow Release | Slow Release | Slow Release | Slow Release | Slow Release |
| APLINDORE free base* (added as fumarate salt) | 4.00% | 2.00% | 0.80% | 0.20% | 0.02% |
| Lactose Fast Flo | 0.00% | 2.00% | 3.20% | 3.80% | 3.98% |
| ProSolv HD 90 | 20.50% | 20.50% | 20.50% | 20.50% | 20.50% |
| Methocel K4M, Prem CR | 40.00% | 40% | 40.00% | 40.00% | 40.00% |
| Methocel K100LV Prem CR LH | 35.10% | 35.10% | 35.10% | 35.10% | 35.10% |
| Mg stearate | 0.40% | 0.40% | 0.40% | 0.40% | 0.40% |

TABLE 12-continued

Aplindore Slow-Release Formulation (core tablets)

| Compositions | | | | |
|---|---|---|---|---|
| aplindore | aplindore | aplindore quantity | aplindore | aplindore |
| 10.0 mg | 5.0 mg | 2.0 mg type | 0.5 mg | 0.05 mg |
| Slow Release | Slow Release | Slow Release | Slow Release | Slow Release |

| | | | | |
|---|---|---|---|---|
| Total | | 100% | 100% | 100% | 100% |
| Total Tablet Weight | | 250 mg | 250 mg | 250 mg | 250 mg |

*Aplindore at 72.8% potency. Actual amount is based on actual potency of aplindore. Corresponding adjustment with ProSolv HD 90 is made.

Exemplary Method for Preparing Medium-Release Core Tablets:

In one exemplary method for preparing medium-release core tablets, the following steps are performed:

1. Screen the aplindore fumarate into a bag. Rinse the container that held the aplindore fumarate with portions of Lactose fast flow, passing through a screen into the bag in step #1.
2. Pass a portion of Lactose fast flow through a screen into the bag and bag blend.
3. Pass a portion of Lactose fast flow through a screen into the bag and bag blend.
4. Transfer the blend into an appropriate size tumble-type blender.
5. Rinse the bag with two portions of Lactose fast flow and add to blender and blend. Pass the Lactose fast flow through a screen prior to adding to the bag.
6. Screen the rest of Lactose fast flow into the blender and blend.
7. Screen Avicel PH 301, Methocel K4M Premium CR and Methocel K100LV Premium CR LH into the blender and blend.
8. Screen the Magnesium Stearate and blend with an approximately equal portion of blend from step #8 and add into the blender and blend.
9. Compress tablets from the final blend from step #9 to a target weight of 250 mg.

Exemplary Method for Preparing Slow-Release Core Tablets

In one exemplary method for preparing medium-release core tablets, the following steps are performed:

1. Screen the aplindore fumarate into a bag.
2. Rinse the container that held the aplindore fumarate with portions of ProSolv HD 90, passing through a screen into the bag in step #1.
3. Pass a portion of ProSolv HD 90 through a screen into the bag and bag blend.
4. Pass a portion of ProSolv HD 90 through a screen into the bag and bag blend. Then transfer the blend into an appropriate size tumble-type blender.
5. Rinse the bag from step #4 with Lactose Monohydrate, previously screened through a screen, and into the blender.
6. Rinse the bag with a portion of ProSolv HD 90 and add to blender and blend. Pass the ProSolv HD 90 through a screen prior to adding to the bag.
7. Screen the rest of ProSolv HD 90 into the blender and blend.
8. Screen Methocel K4M Premium CR and Methocel K100LV Premium CR LH into the blender and blend.
9. Screen the Magnesium Stearate and blend with an approximately equal portion of blend from step #8 and add into the blender and blend.
10. Compress tablets from the final blend from step #9 to a target weight of 250 mg.

*Note: for higher doses, the geometric dilution steps are less.

In some embodiments, the process is a dry blending and direct compression. In further processes, a dry granulation process consisting of slugging and mill or roller compaction and milling can be used, or, preferably, a dry granulation to improves flow properties of the blend. In further embodiments, a wet granulation process can also be used. However, this is not generally preferred because of possible sensitivity of active compound to moisture, and the possible degradation to form an insoluble hydrate. The tablets can be coated or uncoated.

Example 10

Human Absorption and Tolerability Study

A human clinical study was conducted as a multiple dose study of two controlled release formulations of aplindore fumarate, a slow-release (SR) formulation and a medium-release (MR) formulation. Thirty-two (32) subjects were enrolled and 31 completed the study. Subjects were randomly assigned to receive one of the two formulations or placebo. Twelve subjects received aplindore fumarate SR, 12 subjects aplindore fumarate MR, and 8 subjects placebo. Subjects were titrated from 0.05-mg to 5.0-mg on days 1 to 12. On days 12 to 16, subjects fasted before receiving the test article (5.0-mg doses twice per day (BID)). On day 16, a full 24-hour pharmacokinetic profile was taken after AM dose under fasting conditions. On days 17 to 21, subjects received a medium fat meal 30 minutes before test article administration (5.0-mg doses BID), and on day 21 a full 24-hour pharmacokinetic profile was taken.

Table 13 summarizes the pharmacokinetic profile of aplindore fumarate SR 5.0-mg BID and aplindore fumarate MR 5.0-mg BID under fed and fasted conditions and the results from the same dose of APLINDORE IR (5.0-mg) in patients in a separate study.

TABLE 13

Pharmacokinetic Parameters for Aplindore Fumarate Sustained Release Matrix Tablets in Human.
Table 13 - Pharmacokinetic Parameters for Aplindore Fumarate Sustained Release Matrix Tablets in Human.

| Treatment | | $C_{max}$ (pg/mL) | $t_{max}$ (h) | $t_{1/2}$ (h) | $AUC_{ss}$, 0-12 (pg * h/mL) |
|---|---|---|---|---|---|
| Aplindore SR 5.0-mg BID | | | | | |
| Fasted (Day 16) | Mean ± SD | 9229 ± 2488 | 2.1 ± 0.9 | 7.1 ± 3.3 | 67135 ± 20634 |
| | % CV | 26.7% | 43.9% | 45.7% | 30.7% |
| Fed (Day 21) | Mean ± SD | 9267 ± 2533 | 3.5 ± 1.5 | 7.1 ± 5.0 | 65586 ± 19486 |
| | % CV | 27.3% | 43.1% | 45.7% | 29.7% |
| Aplindore MR 5.0-mg BID | | | | | |
| Fasted (Day 16) | Mean ± SD | 8065 ± 2218 | 1.8 ± 0.8 | 5.9 ± 2.0 | 53937 ± 9447 |
| | % CV | 27.5% | 46.1% | 33.2% | 17.5% |
| Fed (Day 21) | Mean ± SD | 8653 ± 2332 | 2.7 ± 1.3 | 5.9 ± 2.0 | 56587 ± 13170 |
| | % CV | 27.0% | 48.6% | 34.4% | 23.3% |
| aplindore fumarate IR 5.0-mg BID | | | | | |
| Patients Fasted (Day 25) | Mean ± SD | 24267 ± 6778 | 0.7 ± 0.3 | 8.0 ± 3.6 | 49552 ± 26524 |
| | % CV | 27.9% | 38.7% | 44.7% | 53.5% |

Following administration of both aplindore MR and aplindore SR, aplindore was absorbed more slowly with mean $t_{max}$ ranging from 1.8 to 3.5 hours, compared to 0.7 hours for aplindore instant release (IR).

Under fasted conditions, MR and SR have similar concentrations and pharmacokinetic parameters with SR providing slightly higher concentrations. The mean $C_{max}$ for SR was 9229 pg/ml compared to 8065 pg/ml for MR. The AUCss for SR is approximately 25% higher than the AUCss for MR.

Similar results are found under fed conditions (SR $C_{max}$≈9267 pg/ml and MR $C_{max}$≈8653 pg/ml). The total exposure is only 15% higher in SR over MR.

Both of the controlled release formulations provide different pharmacokinetic profiles than aplindore fumarate IR 5.0-mg. $C_{max}$ of SR and MR is approximately one-third the $C_{max}$ of IR, and the $t_{max}$ has been prolonged by 1 to 2 hours. Surprisingly, the total exposure (AUC55) is higher for the two sustained-release formulations (~66,000 pg*h/ml in SR, ~55,000 pg*h/ml in MR, vs. ~49,500 pg*h/ml in IR) and the variability in aplindore $AUC_{ss}$ is lower for the MR and SR formulations than the IR formulation.

The side effect profile suggests that the SR and MR formulations are much better tolerated than the immediate release formulations.

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A controlled release oral dosage formulation comprising:
    about 0.05 mg to about 10 mg aplindore, or a pharmaceutically acceptable salt thereof;
    about 0% to about 1.4% lubricant;
    about 10% to 40% saccharide-based diluent;
    one or more release-rate controlling polymers or release-retarding materials selected from the group consisting of:
        about 10% to about 60% wax matrix;
        about 5% to about 40% polyethylene oxide matrix;
        about 15% to about 80% hydroxypropyl methyl cellulose;
    wherein the aplindore, or the pharmaceutically acceptable salt thereof, is released at a rate effective to provide:
        a $C_{max}$ that about 4,000 pg/mL to about 14,000 pg/mL;
        a $T_{max}$ of about 1.5 hours to about 6.3 hours;
        an $AUC_{0-12}$ of about 36,000 pg*h/mL to about 109,000 pg*h/mL; and
    wherein the controlled release oral dosage formulation comprises a tablet, an encapsulated dosage form, one or more microparticles, powder, or a combination thereof.

2. The controlled release oral dosage formulation of claim 1, wherein the aplindore, or the pharmaceutically acceptable salt thereof, is released at a rate effective to provide a $C_{max}$ that is less than about 0.60 times a $C_{max}$ of an instant release formulation.

3. The controlled release oral dosage formulation of claim 1, wherein the aplindore, or the pharmaceutically acceptable salt thereof, is released at a rate effective to provide a $C_{max}$ that is less than about 0.50 times a $C_{max}$ of an instant release formulation.

4. The controlled release oral dosage formulation of claim 1, wherein the aplindore, or the pharmaceutically acceptable salt thereof, is released at a rate effective to provide a $C_{max}$ that is less than about 0.40 times a $C_{max}$ of an instant release formulation.

5. The controlled release oral dosage formulation of claim 1, wherein the aplindore, or the pharmaceutically acceptable salt thereof; is released at a rate to provide an $AUC_{0-12}$ of at least about 1.05 times that of an instant release formulation.

6. The controlled release oral dosage formulation of claim 1, wherein the aplindore, or the pharmaceutically acceptable salt thereof, is released at a rate to provide an $AUC_{0-12}$ of at least about 1.1 times that of an instant release formulation.

7. The controlled release oral dosage formulation of claim 1, wherein the aplindore, or the pharmaceutically acceptable salt thereof, is released at a rate to provide an $AUC_{0-12}$ of at least about 1.2 times that of an instant release formulation.

8. The controlled release oral dosage formulation of claim 1, wherein said about 15% to about 80% hydroxypropylmethyl cellulose is comprised of: about 30% to about 60% low-viscosity hydroxypropyl methyl cellulose, and about 30% to about 60% high-viscosity hydroxypropylmethyl cellulose.

9. The controlled release oral dosage formulation of claim 8, wherein said high viscosity hydroxypropylmethyl cellulose has a viscosity of about 2,663 mPa·s to about 4,970 mPa·s; and wherein said low viscosity hydroxypropylmethyl cellulose has a viscosity of about 80 mPa·s to about 120 mPa·s.

10. The controlled release oral dosage formulation of claim 1, containing about 5 mg of aplindore, or a pharmaceutically acceptable salt thereof, which provides a $C_{max}$ from about 4000 pg/mL to about 14000 pg/mL.

11. The controlled release oral dosage formulation of claim 10, wherein said $C_{max}$ is from about 6000 pg/mL to about 12000 pg/mL.

12. The controlled release oral dosage formulation of claim 5, containing about 5 mg of aplindore, or a pharmaceutically acceptable salt thereof; which provides an $AUC_{0-12}$ from about 36000 pg*h/mL to about 109000 pg*h/mL.

13. The controlled release oral dosage formulation of claim 12, wherein said $AUC_{0-12}$ is from about 36000 pg*h/mL to about 75000 pg*h/mL.

14. The controlled release oral dosage formulation of claim 1, wherein the pharmaceutically acceptable salt is aplindore fumarate.

15. The controlled release oral dosage formulation of claim 1, containing from about 0.05 mg to about 10 mg of aplindore free base added as fumarate salt.

16. The controlled release oral dosage formulation of claim 15, containing 0.05, 0.1, 0.2, 0.25, 0.3, 0.4, 0.5, 0.6, 0.75, 1, 1.5, 2, 3, 4, 5, 6, 8, or 10 milligrams of aplindore free base, added as fumarate salt.

17. The controlled release oral dosage formulation of claim 15, containing 0.05, 0.2, 0.5, 2, or 5 milligrams of aplindore free base, added as fumarate salt.

18. A method of treating a disorder of the dopaminergic system comprising administering to a patient in need of such treatment an effective amount of a controlled release oral dosage formulation according to claim 1.

19. A method of treating a disorder of the dopaminergic system comprising administering to a patient in need of such treatment the unit dosage form of claim 15.

20. A method of treating a disorder of the dopaminergic system comprising administering to a patient in need of such treatment the unit dosage form of claim 17.

21. A controlled release oral dosage formulation comprising aplindore, or a pharmaceutically acceptable salt thereof;
wherein the aplindore, or the pharmaceutically acceptable salt thereof of the controlled release oral dosage formulation, is released at a rate effective to provide a $C_{max}$ of about 4,000 pg/mL to about 14,000 pg/mL; and wherein the aplindore, or the pharmaceutically acceptable salt thereof of the controlled release oral dosage formulation is released at a rate to provide an $AUC_{0-12}$ of about 36,000 pg*h/mL to about 109,000 pg*h/mL; and
wherein the controlled release oral dosage formulation comprises a microparticle wherein the microparticle comprises an inert core; a layer comprising the aplindore or the pharmaceutically acceptable salt thereof disposed on the inert core; and a coating comprising at least one release rate controlling polymer disposed on the layer of the compound; or wherein the controlled release oral dosage formulation comprises a microparticle, wherein the microparticle comprises a core that comprises the aplindore or the pharmaceutically acceptable salt thereof and at least one release rate controlling polymer; and a coating layer disposed on the core wherein the coating layer optionally comprises at least one release rate controlling polymer.

22. The controlled release oral dosage formulation of claim 21, wherein the controlled release oral dosage formulation comprises a microparticle wherein the microparticle comprises an inert core; a layer comprising the aplindore or the pharmaceutically acceptable salt thereof disposed on the inert core; and a coating comprising at least one release rate controlling polymer disposed on the layer of the compound; and wherein the at least one release rate controlling polymer of the coating is selected from: Eudragit RS, Eudragit RL, Surelease, and combinations of two or more thereof.

23. The controlled release oral dosage formulation of claim 21, wherein the controlled release oral dosage formulation comprises a microparticle, wherein the microparticle comprises a core that comprises the aplindore or the pharmaceutically acceptable salt thereof and at least one release rate controlling polymer; and a coating layer disposed on the core wherein the coating layer optionally comprises at least one release rate controlling polymer; wherein the at least one release rate controlling polymer of the core is a hydroxypropyl methyl celluloses; and wherein the at least one release rate controlling polymer of the coating is selected from: Eudragit RS, Eudragit RL, Surelease, and combinations of two or more thereof.

24. The controlled release oral dosage formulation of claim 21, wherein the aplindore, or the pharmaceutically acceptable salt thereof, is released at a rate effective to provide a $C_{max}$ that is less than about 0.60 times a $C_{max}$ of an instant release formulation.

25. The controlled release oral dosage formulation of claim 21, wherein the aplindore, or the pharmaceutically acceptable salt thereof, is released at a rate effective to provide a $C_{max}$ that is less than about 0.50 times a $C_{max}$ of an instant release formulation.

26. The controlled release oral dosage formulation of claim 21, wherein the aplindore, or the pharmaceutically acceptable salt thereof, is released at a rate effective to provide a $C_{max}$ that is less than about 0.40 times a $C_{max}$ of an instant release formulation.

27. The controlled release oral dosage formulation of claim 21, wherein the pharmaceutically acceptable salt is aplindore fumarate.

28. A method of treating a disorder of the dopaminergic system comprising administering to a patient in need of such treatment an effective amount of a controlled release oral dosage formulation according to claim 21.

* * * * *